United States Patent [19]

Curran

[11] 3,992,383
[45] Nov. 16, 1976

[54] PROCESS FOR PREPARING PYRIDINE DERIVATIVES

[75] Inventor: Adrian Charles Ward Curran, Newcastle-upon-Tyne, England

[73] Assignee: John Wyeth & Brother Limited, Maidenhead, England

[22] Filed: Nov. 22, 1974

[21] Appl. No.: 526,354

[30] Foreign Application Priority Data

Dec. 17, 1973 United Kingdom............... 58308/73

[52] U.S. Cl.......................... 260/283 S; 260/279 R; 260/283 R; 260/288 CF; 260/290 R; 260/290 HL; 260/294.8 B; 260/294.8 C; 424/258

[51] Int. Cl.².............. C07D 215/40; C07D 219/08; C07D 221/16

[58] Field of Search....... 260/283 S, 288 CF, 288 R, 260/286 R, 294.8 B, 294.8 C, 279 R

[56] References Cited
UNITED STATES PATENTS 3,745,162  7/1973  Helsley .......................... 260/283 D

FOREIGN PATENTS OR APPLICATIONS 2,352,585  5/1974  Germany......................... 260/283 S

OTHER PUBLICATIONS

Migrdichian; Chem. of Organic Cyanogen Compounds; p. 260; (1947).
Barnikow Chem. Abstr., vol. 66; p. 10712d, (1967).
Fieser et al.; Advanced Organic Chemistry; p. 783, (1961).
Hagelloch et al.; Leit. Naturforschg; vol. 6b; pp. 147–155, (1951).

*Primary Examiner*—Nicholas S. Rizzo
*Assistant Examiner*—Mary C. Vaughn

[57] ABSTRACT

The invention concerns a novel process for preparing 5,6,7,8-tetrahydroquinolines and related compounds substituted by a monosubstituted thioamide group in which a metal derivative of the 5,6,7,8-tetrahydroquinoline or related compound is reacted with an alkyl, aryl or aralkyl isothiocyanate and the product is treated with hydrogen ions.

12 Claims, No Drawings

PROCESS FOR PREPARING PYRIDINE DERIVATIVES

The invention relates to processes for preparing pyridine derivatives.

The process of the present invention relates to the preparation of compounds of formula I,

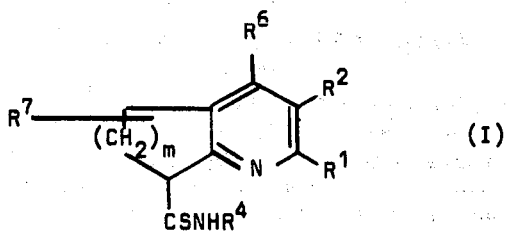

and acid addition salts thereof, wherein $R^1$, $R^2$ and $R^6$ are the same or different and represent hydrogen, trifluoromethyl, or an alkyl, aralkyl or aryl radical, any of which radicals may be substituted by alkyl, alkoxy, nitro or trifluoromethyl or $R^1$ and $R^2$ taken together represent an alkylene chain $-CH_2(CH_2)_nCH_2-$ wherein n is 1, 2 or 3, $R^7$ represents single or multiple substitution by hydrogen, or alkyl, aralkyl or aryl radicals any of which radicals may be substituted by alkyl, alkoxy, nitro or trifluoromethyl and when $R^1$ and $R^2$ taken together form an alkylene chain the resulting ring may be substituted by one or more $R^7$ radicals as defined above, m is 1, 2 or 3 and $R^4$ is an alkyl, aralkyl or aryl radical.

Compounds of formula I, in which $R^4$ is an alkyl or aralkyl radical either of which radicals may be substituted by alkyl, alkoxy, nitro or trifluoromethyl and including tricylic compounds when m and n are equal are described in copending U.S. Ser. No. 460,265 filed Apr. 11, 1974, now abandoned, which is a continuation-in-part of U.S. Ser. No. 403,289 now abandoned. They find use as anti-ulcer agents or intermediates therefor.

Accordingly the present invention provides a process for preparing a compound of formula I as defined above, which process comprises treating a compound of formula II.

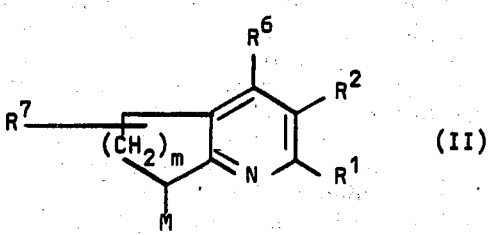

where $R^1$, $R^2$, $R^6$, $R^7$ and m are as defined in connection with formula I above, and M is sodium, potassium, lithium, or MgHal, where Hal is chlorine, bromine or iodine, with a compound of formula $R^4NCS$ wherein $R^4$ is as defined in connection with formula I and treating the product with hydrogen ions.

Preferably a starting material of formula II, wherein M is lithium of MgHal e.g. MgBr is used. Conveniently the product after reaction with $R^4NCS$ is treated with acid, e.g. an aqueous mineral acid such as a hydrohalic acid preferably hydrochloric acid. Alternatively, any other proton source may be used e.g. water or an alcohol e.g. a lower alkanol such as methanol or ethanol, or acetic acid.

Starting material of formula II, wherein M is MgHal may be prepared by treating a compound of formula II, wherein M is hydrogen, with an alkyl magnesium halide $R^{11}MgHal$ wherein $R^{11}$ is an alkyl group, preferably a lower alkyl group of 1 to 6 carbon atoms, and Hal is chlorine, bromine or iodine. $R^{11}$ may be a straight or branched chain alkyl group, the isopropyl group being preferred. The reaction is conducted in an inert atmosphere preferably in an inert solvent with a boiling point in the range 100° – 120° C e.g. toluene of dioxan.

Starting materials of formula II, wherein M is MgHal are described in copending U.S. Ser. No. 526,353, filed Nov. 22, 1974. The other starting materials of formula II are described in U.S. Ser. No. 460,265, now abandoned. Compounds of formula II where M is other than MgHal may be prepared by reacting a corresponding compound of formula IV

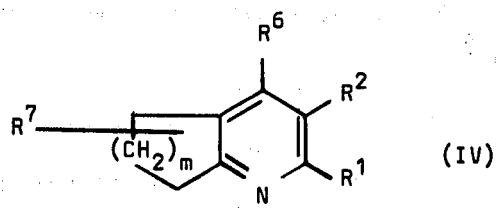

with a metal alkyl e.g. $MR^{10}$ wherein M is sodium, potassium or lithium and $R^{10}$ is alkyl, aryl or aralkyl or $M(R^{10})_2$ wherein M is calcium or magnesium and $R^{10}$ is as previously defined.

When any of $R^1$, $R^2$, $R^4$, $R^6$ or $R^7$ is an alkyl radical it is preferred that this is a lower alkyl radical which may be a straight or branched chain, having from 1 to 6 carbon atoms, e.g. methyl, ethyl, n- and iso-propyl and n-, s- and t-butyl, $R^7$ may be a gem-dimethyl group and when a single radical may be on the same carbon atom as the group X. The term alkyl radical is also intended to embrace cyclic alkyl radicals e.g. cyclobutyl, cyclopentyl and cyclohexyl. When any of $R^1$, $R^2$, $R^6$ or $R^7$ is an aralkyl radical it is preferred that this is an aryllower alkyl radical where the lower alkyl portion may be as discussed above for a lower alkyl radical. The aryl portion is preferably a phenyl radical.

When any of $R^1$, $R^2$, $R^4$, $R^6$ or $R^7$ is an aryl radical, this is preferably phenyl or a substituted phenyl radical (substituted by alkyl, alkoxy, nitro or trifluoromethyl). However, other aryl radicals which may be used include naphthyl.

Preferably $R^1$, $R^2$ and $R^6$ are selected from hydrogen and lower alkyl and $R^7$ is hydrogen. More preferably one of $R^1$, $R^2$ and $R^6$ is lower alkyl e.g. methyl and the others are hydrogen and $R^7$ is hydrogen. Preferably $R^4$ is a lower alkyl radical with from 1 to 6 carbon atoms e.g. 1 – 4 carbon atoms.

It has been found that the desired compound of formula I, may be accompanied by a bisthioamide of formula III

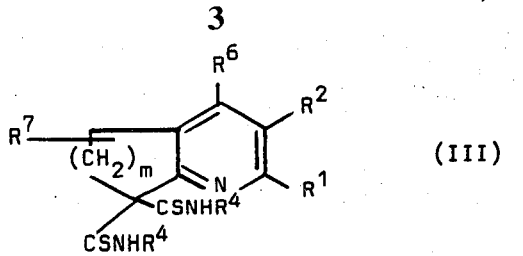

wherein $R^1$, $R^2$, $R^4$, $R^7$ and $m$ are as defined in connection with formula I. Such bisthioamides can usually be removed by fractional crystallisation.

The invention also includes a process for preparing a compound of formula I as defined above which process comprises treating a corresponding compound of formula IV as defined above, with a compound of formula R MgHal where Hal is chlorine bromine of iodine and R is an alkyl, aryl or aralkyl group of a metal alkyl $MR^{10}$ wherein M is sodium potassium of lithium and $R^{10}$ is alkyl, aryl or aralkyl or $M(R^{10})_2$ wherein M is calcium or magnesium and $R^{10}$ is as defined above, to obtain a metal derivative with an isothiocyanate of formula $R^4NCS$ wherein $R^4$ is an alkyl, aralkyl or aryl radical, and then treating the product with hydrogen ions.

The following examples illustrate the invention, temperatures are in °C.

EXAMPLE 1

3-Methyl-5,6,7,8-tetrahydroquinoline-8-(N-methyl)-thiocarboxamide

A 15% W/W solution of n-butyl lithium in hexane (26ml, 0.06m) was added dropwise to a stirred solution of 3-methyl-5,6,7,8-tetrahydroquinoline (7.3g, 0.05m) in anhydrous ether (50ml) and in an atmosphere of dry nitrogen. After 1 hour at 24° C the reaction mixture was cooled to 0° C and treated dropwise with a solution of methylisothiocyanate (3.8g, 0.05m) in anhydrous ether (10ml) and allowed to stand for 4 hours at 24° C. The cooled reaction mixture was diluted with 2N HCl and the organic layer separated and discarded. The aqueous solution was adjusted to pH 10.0 with sodium carbonate and extracted with ether (3 × 50ml). The combined extracts were washed with brine, dried (MgSO$_4$) and the solvent removed. The residual oily solid was crystallised from iso-propanol to give the title compound as pale yellow needles (3.2g) m.p. 159° C. Found: C, 65.3, H, 7.2; N, 12.5. $C_{12}H_{16}N_2S$ requires: C, 65.4; H, 7.3; N, 12.7%.

EXAMPLE 2

3-methyl-5,6,7,8-tetrahydroquinoline-8(N-phenyl)-thio-carboxamide

A 15% W/W solution of n-butyl lithium in hexane (26Ml.,0.06mol.) was added dropwise, with stirring, cooling to 0° C and under an atmosphere of nitrogen, to a solution of 3-methyl-5,6,7,8-tetrahydroquinoline (7.3g. 0.05mol.) in anhydrous ether (50ml.). The reaction mixture was stirred for an additional 30 minutes at room temperature cooled to 0° C and then treated dropwise with a solution of phenylisothiocyanate (8.1g, 0.06mol.) in anhydrous ether (10ml.) The reaction mixture was stirred for a further 1 hour at room temperature and diluted with 2N HCl (50ml.) and the organic layer separated and discarded. The aqueous phase was adjusted to pH 10.0 with sodium carbonate and extracted with chloroform (3 × 50ml.). The combined extracts were washed with brine, dried (MgSO$_4$) and the solvent removed in vacuo to give a brown oil which yielded the title compound as pale yellow needles (2G, 14%) after chromatography on silica and elution with chloroform followed by recrystallisation (isopropanol) m.pt. 132°. Found: C, 71.97; H, 6.49; N, 9.66%. $C_{17}H_{18}N_2S$. requires: C, 72.3; H, 6.38; N, 9.93%.

EXAMPLE 3

3-methyl-5,6,7,8-tetrahydroquinoline-8-(N-benzyl)-thiocarboxamide

A solution of 3-methyl-5,6,7,8-tetrahydroquinoline (7.3g, 0.05mol.) in anhydrous ether (50ml.) was treated dropwise with stirring, cooling to 0° C and under an atmosphere of nitrogen with a 15% W/W solution of n-butyl lithium in hexane (26Ml., 0.06mol.) and the mixture stirred for a further 30 minutes at room temperature. The mixture was transferred to a dropping funnel and added dropwise with stirring, cooling and in an atmosphere of nitrogen to a solution of benzylisothiocyanate (8.95g, 0.06mol.) in anhydrous ether (50ml.). The reaction mixture was stirred for a further 1 hour at room temperature and then diluted with water (50ml.) and acidified with 2N HCl (50ml.). The solid was filtered and recrystallised from ethanol to give the title compound as the hydrochloride, colourless needles (6g. 38%) m.p. 230° (dec.) Found: C, 65.12; H, 6.49; N, 8.67%. $C_{18}H_{20}N_2S$. HCl requires C, 65.06; H, 6.33; N, 8.44%.

EXAMPLE 4

3-methyl-5,6,7,8-tetrahydroquinoline-8-(N-n-butyl)-thiocarboxamide

A solution of 3-methyl-5,6,7,8-tetrahydroquinoline (7.3g, 0.05mol.) in anhydrous ether (50ml.) was treated dropwise with stirring, cooling to 0° C and in an atmosphere of nitrogen with a 15% W/W solution of n-butyl lithium in hexane (26ml. 0.06mol.) and the mixture stirred for a further 30 minutes at room temperature. The mixture was transferred to a dropping funnel and added dropwise with stirring, cooling and in an atmosphere of nitrogen to a solution of n-butylisothiocyanate (6.95g, 0.06mol.) in anhydrous ether (50ml.). The mixture was stirred at room temperature for an additional 1 hour, diluted with water (50ml.) and acidified with 2N HCl (50ml.) and the aqueous solution was adjusted to pH 10.0 with sodium carbonate and extracted with methylene chloride (3 × 50ml.). The combined extracts were washed with brine, dried (MgSO$_4$) and the solvent removed in vacuo to give a pale yellow oil which was dissolved in anhydrous ether and treated with an excess of ether saturated with HCl gas. The solid was filtered and recrystallised from iso-propanol to give the title compound as the hydrochloride, colourless needless (11.5g. 74%) m.p. 195° C (dec.). Found: C, 60.34; H, 7.79; N, 9.39% $C_{15}H_{22}N_2S$ HCl requires: C, 60.30; H, 7.40; N, 9.3%.

EXAMPLE 5

3-methyl-5,6,7,8-tetrahydroquinoline-8-(N-methyl)-thiocarboxamide 3-methyl-5,6,7,8-tetrahydroquinoline (6.46g, 0.044 mol.) was added portionwise to an ethereal solution of isopropylmagnesium bromide (prepared from magnesium (2.78g, 0.105g. atom), isopropylbromide (10.8g, 0.088mol.) in ether (20 ml.)) in an atmosphere of nitrogen. The reaction mixture was heated to 90° and the ether removed by distillation and toluene (5 ml.) added and the mixture heated at 130° for 2 hours allowing 3 ml. of toluene to distill. The residue (3-methyl-5,6,7,8-tetrahydroquinoline-8-magnesium bromide) was cooled, diluted with ether (30 ml.), decanted from unreacted magnesium and treated dropwise, with cooling, with a solution of methylisothiocyanate (6.46g, 0.088mol.) in ether (10 ml.). The reaction mixture was stirred for an additional 1 hour at room temperature, diluted with 2N HCl (200 ml.) and the organic layer separated and discarded. The aqueous phase was adjusted to pH 10.0 with sodium carbonate and extracted with methylene chloride (2 × 100 ml.). The combined extracts were washed with brine, dried and the solvent removed in vacuo to give a pale yellow oil, which was chromatographed on silica by elution with chloroform to give the title compound as pale yellow needles (2g. 18%) after recrystallisation from isopropanol m.p. 159° C and identical to authentic material.

EXAMPLE 6

3-methyl-5,6,7,8-tetrahydroquinoline-8-(N-phenyl)-thiocarboxamide

The title compound was prepared from 3-methyl-5,6,7,8-tetrahydroquinoline (6.46g, 0.04mol.) and phenylisothiocyanate (11.2g, 0.088mol.) following the procedure of the previous example and was isolated as colourless needles (2g, 20%) after chromatography on silica and elution with chloroform followed by recrystallisation from isopropanol m.p. 132°. The compound was identical to the authentic material.

EXAMPLE 7

5,6,7,8-Tetrahydroquinoline-8-(N-methyl)thiocarboxamide and
5,6,7,8-tetrahydroquinoline-8,8-di[(N-methyl)thiocarboxamide]

A solution of 5,6,7,8-tetrahydroquinoline (6.65g, 0.05 mole) in ether (30 ml) was treated with 9% w/v n-butyl lithium solution in hexane (39.5 ml, 0.055 mole) at 0° C. The reaction mixture was stirred at this temperature for 1 hr. and a solution of methyl isothiocyanate (4.01 g, 0.055 mole) in ether (5 ml) was added dropwise and the stirring was continued for a further hour. Water (5 ml) was added and the mixture acidified with 2N HC1 solution. The acid layer was washed with ethyl acetate, basified with solid sodium carbonate and extracted with chloroform (3 × 100 ml). The chloroform extracts were dried over $MgSO_4$ filtered and evaporated. The residue was triturated with hexane and the resulting solid was recrystallised twice from isopropyl alcohol to give 5,6,7,8-tetrahydroquinoline-8,8-di[N-methyl)thiocarboxamide](2g) which was converted into the hydrochloride in isopropyl alcohol with ethereal HCl m.p. 217° C decomp. (Found: C, 48.7; H, 6.1; N, 12.5. $C_{13}H_{17}N_3S_2$ HCl. 1/4 $H_2O$ requires C, 48.7; H, 5.8; N, 13.1). The mother liquors from the isopropyl alcohol recrystallisations were combined and evaporated to dryness and the residue was extracted with hot hexane leaving a crystalline residue which was recrystallised from isopropyl alcohol to give 5,6,7,8-tetrahydroquinoline-8-(N-methyl)thiocarboxamide (3.5g) which was converted into the hydrochloride with ethereal HCl and recrystallised from isopropyl alcohol m.p. 250° C decomp. (Found: C, 54.5; H, 6.5; N, 11.5. $C_{11}H_{14}N_2S.HCl$ requires C, 54.4; H, 6.2; N, 11.5%.)

EXAMPLE 8

3-Methyl-5,6,7,8-tetrahydroquinoline-8-[N-(3'-phenyl-1-propyl)]-thiocarboxamide

A solution of 3-methyl-5,6,7,8-tetrahydroquinoline (7.3 g, 0.05 mole) in benzene (50 ml) was cooled in ice and treated with a 9% w/v solution of n-butyl lithium (22 ml, 0.047 mole). After stirring for 1 h. at 0° C a solution of 3-phenylpropyl isothiocyanate (8.85 g, 0.05 mole) in benzene (50 ml) was added dropwise followed by stirring for a further hour. Water (5 ml) was added followed by sufficient 2N HCl to make the mixture acidic causing precipitation of a solid which was removed by filtration, washed with water and ether and dried to give 3-methyl-5,6,7,8-tetrahydroquinoline-8-[N-(3'-phenyl-1-propyl)]-thiocarboxamide (3.3 g, 18%) Recrystallisation from isopropyl alcohol gave needles m.p. 238° C decomp. (Found: C, 67.0; H, 7.2; N, 7.8. $C_{20}H_{24}N_2S.$ HCl. requires C, 66.6; H, 7.0; N, 7.8%)

I claim:
1. A process for preparing a compound of formula I

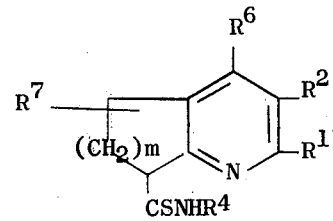

and acid addition salts thereof, wherein $R^1$, $R^2$ and $R^6$ are independently members selected from the group consisting of hydrogen, trifluoromethyl, alkyl of 1 to 6 carbon atoms, phenylalkyl in which the alkyl moiety has 1 to 6 carbon atoms and phenyl; or $R^1$ and $R^2$ taken together are polymethylene of 3 to 5 carbon atoms;

$R^7$ is a member selected from the group consisting of hydrogen, gem-dimethyl, alkyl of 1 to 6 carbon atoms, phenylalkyl in which the alkyl moiety has 1 to 6 carbon atoms, and phenyl;

in which the phenyl group or the phenyl portion of the phenylalkyl group representing $R^1$, $R^2$, $R^6$ or $R^7$ is unsubstituted or in monosubstituted by alkyl of 1 to 6 carbon atoms, alkoxy of 1 to 6 carbon atoms, halogen, nitro or trifluoromethyl;

with the proviso that when $R^1$ and $R^2$ or $R^2$ and $R^6$ are both alkyl, they are selected from normal and secondary alkyl groups;

m is 1, 2 or 3; and $R^4$ is alkyl of 1 to 6 carbon atoms; which process comprises the steps of treating a compound of formula II

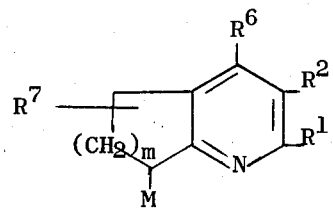

wherein
R¹, R², R⁶, R⁷ and m are as defined in connection with formula I above and M is sodium, potassium, lithium, or MgHal where Hal is chlorine, bromine or iodine, with an isothiocyanate of the formula R⁴NCS wherein R⁴ is as defined in connection with formula I;

treating the product with hydrogen ions.

2. A process which comprises the steps of
a. treating a compound of the formula:

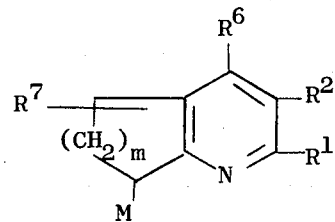

in which M is sodium, potassium, lithium, MgCl, MgBr or MgI; with a compound of the formula:

R⁴NCS in which R⁴ is alkyl of 1 to 6 carbon atoms, in an inert organic solvent, and
b. protonating the product of step (a) to produce a product of the formula:

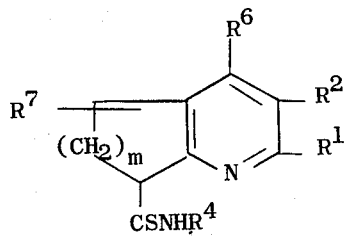

wherein
R¹, R² and R⁶ are, independently, hydrogen, trifluoromethyl, alkyl of 1 to 6 carbon atoms, phenylalkyl in which the alkyl moiety has from 1 to 6 carbon atoms, or phenyl;
R¹ and R², taken together represent a polymethylene chain of 3 to 5 carbon atoms;
R⁷ is hydrogen, alkyl of 1 to 6 carbon atoms, phenylalkyl in which the alkyl moiety has from 1 to 6 carbon atoms, phenyl, or gem-di-n-alkyl in which each alkyl group has from 1 to 6 carbon atoms;
any phenyl moiety being unsubstituted or monosubstituted by alkyl of 1 to 6 carbon atoms, alkoxy of 1 to 6 carbon atoms, halo, nitro or trifluoromethyl;
and
m is 1, 2 or 3,
providing that when R¹ and R² or R² and R⁶ are both alkyl, they are normal or secondary alkyl groups.

3. A process which comprises the steps of:
a. treating a compound of the formula:

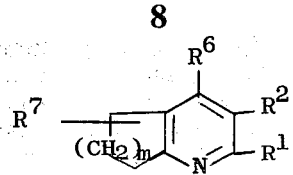

with a compound selected from the group consisting of RMgHal, NaR¹⁰, LiR¹⁰, Ca(R¹⁰)₂ and Mg(R¹⁰)₂ in which R and R¹⁰ are alkyl, aryl or aralkyl and Hal is chlorine, bromine or iodine to produce a compound of the formula:

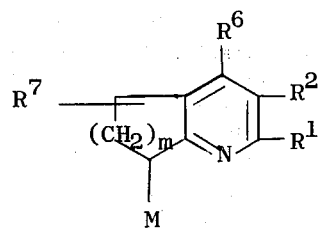

in which
M is Na, Li, CaR¹⁰, MgR¹⁰, MgCl, MgBr or MgI;
b. reacting the product of step (a) with a compound of the formula:

R⁴NCS in which R⁴ is alkyl of 1 to 6 carbon atoms, in an inert organic solvent;
c. protonating the product of step (b) and
d. recovering from step (c) a compound of the formula:

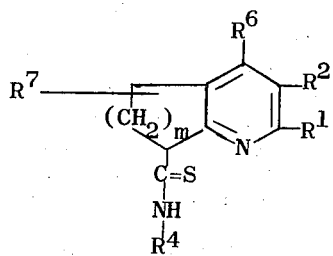

in which
R¹, R² and R⁶ are, independently, hydrogen, trifluoromethyl, alkyl of 1 to 6 carbon atoms, phenylalkyl in which the alkyl moiety has from 1 to 6 carbon atoms, or phenyl;
R¹ and R², taken together represent a polymethylene chain of 3 to 5 carbon atoms;
R⁷ is hydrogen, alkyl of 1 to 6 carbon atoms, phenylalkyl in which the alkyl moiety has from 1 to 6 carbon atoms, phenyl, or gem-di-n-alkyl in which each alkyl group has from 1 to 6 carbon atoms; and
m is 1, 2 or 3.

4. A process for the production of a compound of the formula:

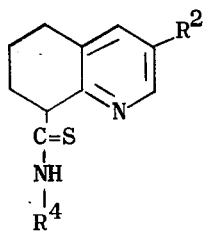

in which
R² is hydrogen or alkyl of 1 to 6 carbon atoms, and R⁴ is alkyl of 1 to 6 carbon atoms,
which comprises the steps of
a. reacting a compound of the formula:

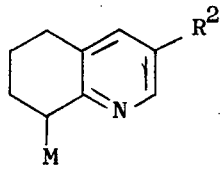

in which
M is Na, K, Li, MgCl, MgBr or MgI
with an isocyanate of the formula R⁴NCS and
b. protonating the product.

5. The process of claim 2, in which M is Li or MgBr.

6. The process of claim 2, in which protonation is effected with an aqueous mineral acid.

7. The process of claim 2, in which R⁴ is alkyl of 1 to 6 carbon atoms.

8. The process of claim 7, in which R⁴ is methyl.

9. The process of claim 2 in which the initial reactant is bicyclic.

10. The process of claim 9 in which the initial reactant is a 5, 6, 7, 8 - tetrahydroquinoline.

11. The process of claim 2, in which R¹, R² and R⁶ are independently hydrogen or methyl and R⁷ is hydrogen.

12. The process of claim 3 in which R¹, R² and R⁶ are, independently, hydrogen or alkyl of 1 to 6 carbon atoms and R⁷ is hydrogen.

\* \* \* \* \*